United States Patent [19]

Sapia

[11] Patent Number: Plant 7,054

[45] Date of Patent: Nov. 7, 1989

[54] CARNATION PLANT NAMED MILLY

[76] Inventor: Flavio Sapia, Via Ducca Degli Abrozzi (Strada Viletta), San Remo, Italy

[21] Appl. No.: 260,377

[22] Filed: Oct. 18, 1988

[51] Int. Cl.[4] ..... A01H 5/00
[52] U.S. Cl. ..... Plt./71
[58] Field of Search ..... Plt./71

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A carnation plant named Milly particularly characterized by its flat flower form; semi-double flower type; medium pink flower color; diameter across face of capitulum of 40 to 55 mm at maturity; medium flowering response of 13 to 17 weeks after planting in year round flowerings; upright semi-compound spray formation; short plant height of 20 to 25 cm in a 10 cm pot with no growth regulators; bushy growth at base of plant; and recommended for pot spray carnation culture only.

1 Drawing Sheet

The present invention comprises a new and distinct cultivar of carnation, botanically known as *Dianthus caryophyllus*, L. and referred to by the cultivar name Milly.

Milly was originated from a cross made by the inventor, Flavio Sapia, in a controlled breeding program in San Remo, Italy, in July 1983. The female parent and the male parent of Milly were both unnamed seedlings.

Milly was discovered and selected as one flowering plant within the progeny of the stated cross by the inventor in December 1984, in a controlled environment in San Remo, Italy.

The first act of asexual reproduction of Milly was accomplished when vegetative cuttings were taken by the inventor from the initial selection in March of 1985 in a controlled environment in San Remo, Italy. Horticultural examination of controlled flowerings of successive plantings has shown that the unique combination of characteristics as herein disclosed for Milly are firmly fixed and are retained through successive generations of asexual reproduction.

Milly has not been observed under all possible environmental conditions. The phenotype may vary significantly with variations in environment such as temperature, light intensity and daylength.

The following observations, measurements and comparisons describe plants grown in Salinas, Calif., under greenhouse conditions which approximate those generally used in commercial greenhouse practice.

The following traits have been repeatedly observed and are determined to be basic characteristics of Milly, which, in combination, distinguish this carnation as a new and distinct cultivar:

1. Flat flower form.
2. Semi-double flower type.
3. Medium pink flower color.
4. Diameter across face of capitulum of 40 to 55 mm at maturity.
5. Medium flowering response of 13 to 17 weeks after planting in year round flowerings.
6. Upright semi-compound spray formation.
7. Short plant height of 20 to 25 cm in a 10 cm pot with no growth regulators.
8. Bushy growth at base of plant.
9. Recommended for pot spray carnation culture only.

The accompanying color photographic drawing shows typical inflorescence and leaf characteristics of Milly, with the colors being as nearly true as possible with illustrations of this type. The photograph illustrates Milly grown as a pot spray carnation in a 10 cm pot.

The culture of pot spray carnations is a relatively new method of cultivating carnations, and there are no commercial cultivars known to the inventor which are similar in comparison to Milly.

In the following description, color references are made to The Royal Horticultural Society Colour Chart. The color values were taken Dec. 12, 1987 on plant material grown in Salinas, Calif.

Classification:

*Botanical.*—*Dianthus caryophyllus,* L. cv. Milly.
*Commercial.*—Pot spray carnation.

INFLORESCENCE

A. Flower:
*Form.*—Flat.
*Type.*—Semi-double, up to 22 petals.
*Diameter across face.*—40 to 55 mm at maturity.

B. Corolla color:
*General tonality from a distance of three meters*.—Medium pink.
*Color* (*upper surface*).—55C to 55D, fading to 56C to 56D.
*Color* (i under surface).—56C to 56D.

C. Reproductive organs:
*Androecium.*—Typical carnation. Medium filament length, 20 to 25 mm. Anthers are degenerated, no pollen.
*Gynoecium.*—Typical carnation. White pistil, distal portion tinged with 63B. Pistil length up to 30 mm.

PLANT

A. General appearance:
*Height.*—Short plant height of 20 to 25 cm in a 10 cm pot with no growth regulators.
*Growth.*—Bushy at base of plant.

B. Foliage: Typical carnation. Abundant at base of plant.
*Color* (*upper surface*).—Closest to 137A.
*Color* (*under surface*).—Closest to 137B to 137C.

I claim:

1. A new and distinct carnation plant named Milly, as described and illustrated.

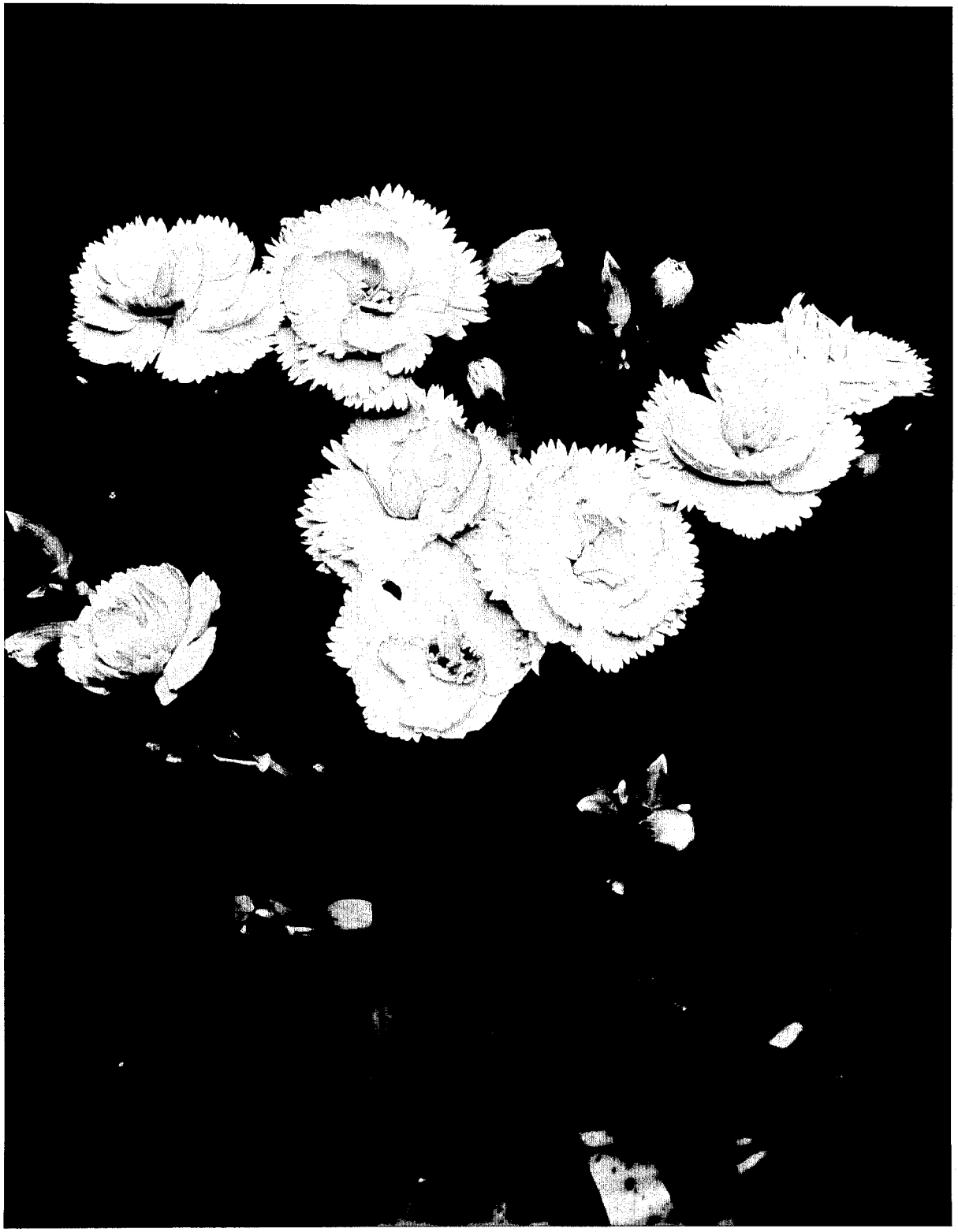

* * * * *